United States Patent
Fuchs et al.

(10) Patent No.: US 7,840,248 B2
(45) Date of Patent: Nov. 23, 2010

(54) ONLINE SOURCE RECONSTRUCTION FOR EEG/MEG AND ECG/MCG

(75) Inventors: Manfred Fuchs, Hamburg (DE); Stephen F. Sands, El Paso, TX (US)

(73) Assignee: Compumedics Limited, Thomastown (AU)

( * ) Notice: Subject to any disclaimer, the term of this patent is extended or adjusted under 35 U.S.C. 154(b) by 0 days.

(21) Appl. No.: 10/765,320

(22) Filed: Jan. 27, 2004

(65) Prior Publication Data
US 2005/0059874 A1    Mar. 17, 2005

Related U.S. Application Data

(60) Provisional application No. 60/443,234, filed on Jan. 27, 2003.

(51) Int. Cl.
*A61B 5/05* (2006.01)
(52) U.S. Cl. .................. 600/407; 600/409; 324/307; 324/309
(58) Field of Classification Search .......... 600/407, 600/409; 324/307, 309
See application file for complete search history.

(56) References Cited

U.S. PATENT DOCUMENTS

| | | | |
|---|---|---|---|
| 4,516,579 A | | 5/1985 | Irnich |
| 4,974,602 A | * | 12/1990 | Abraham-Fuchs et al. .. 600/544 |
| 5,029,082 A | * | 7/1991 | Shen et al. .................. 600/512 |
| 6,073,040 A | * | 6/2000 | Kiyuna ....................... 600/409 |
| 6,187,032 B1 | * | 2/2001 | Ohyu et al. ................. 600/409 |
| 7,092,748 B2 | * | 8/2006 | Valdes Sosa et al. ........ 600/407 |
| 2003/0018277 A1 | | 1/2003 | He |

FOREIGN PATENT DOCUMENTS

| | | |
|---|---|---|
| DE | 195 23 771 A | 3/1996 |
| EP | 0 983 747 A | 3/2000 |

OTHER PUBLICATIONS

Fuchs M et al: "Improving source reconstructions by combining bioelectric and biomagnetic data" Mar. 1998.*
Braun et al., "Confidence interval of single dipole locations based on EEG data," Brain Topography, Human Sciences Press, New York, NY, 10:1, 31-37 (1997).
Yamazyki et al., "The accuracy of localizing equivalent dipoles and the spatio-temporal correlations of background EEG," IEEE Transactions on Biomedical Engineering, 45:9, 1114-1121 (1998).

* cited by examiner

*Primary Examiner*—Brian Casler
*Assistant Examiner*—John F Ramirez
(74) *Attorney, Agent, or Firm*—Sughrue Mion, PLLC

(57) ABSTRACT

In one embodiment, the present invention includes an EEG system comprising of sensors which are utilized to gather an electromagnetic signal from a patient; a signal processing system; and a computer system. The computer system is configured to support multiple threads of execution. The computer system initiates a first thread of execution, a measurement module, where the data is filtered and in some cases averaged. Typically, the data is filtered for a particular latency period. Once the data has been filtered and averaged, the result is given to a second thread of execution, the source reconstruction module, which then proceeds to generate a source reconstruction for the trial. The measurement module then acquires and processes new electromagnetic data from a new trial while the source reconstruction is being performed on the most recent trial.

5 Claims, 2 Drawing Sheets

US 7,840,248 B2

ONLINE SOURCE RECONSTRUCTION FOR EEG/MEG AND ECG/MCG

PRIOR HISTORY

Figure 1:
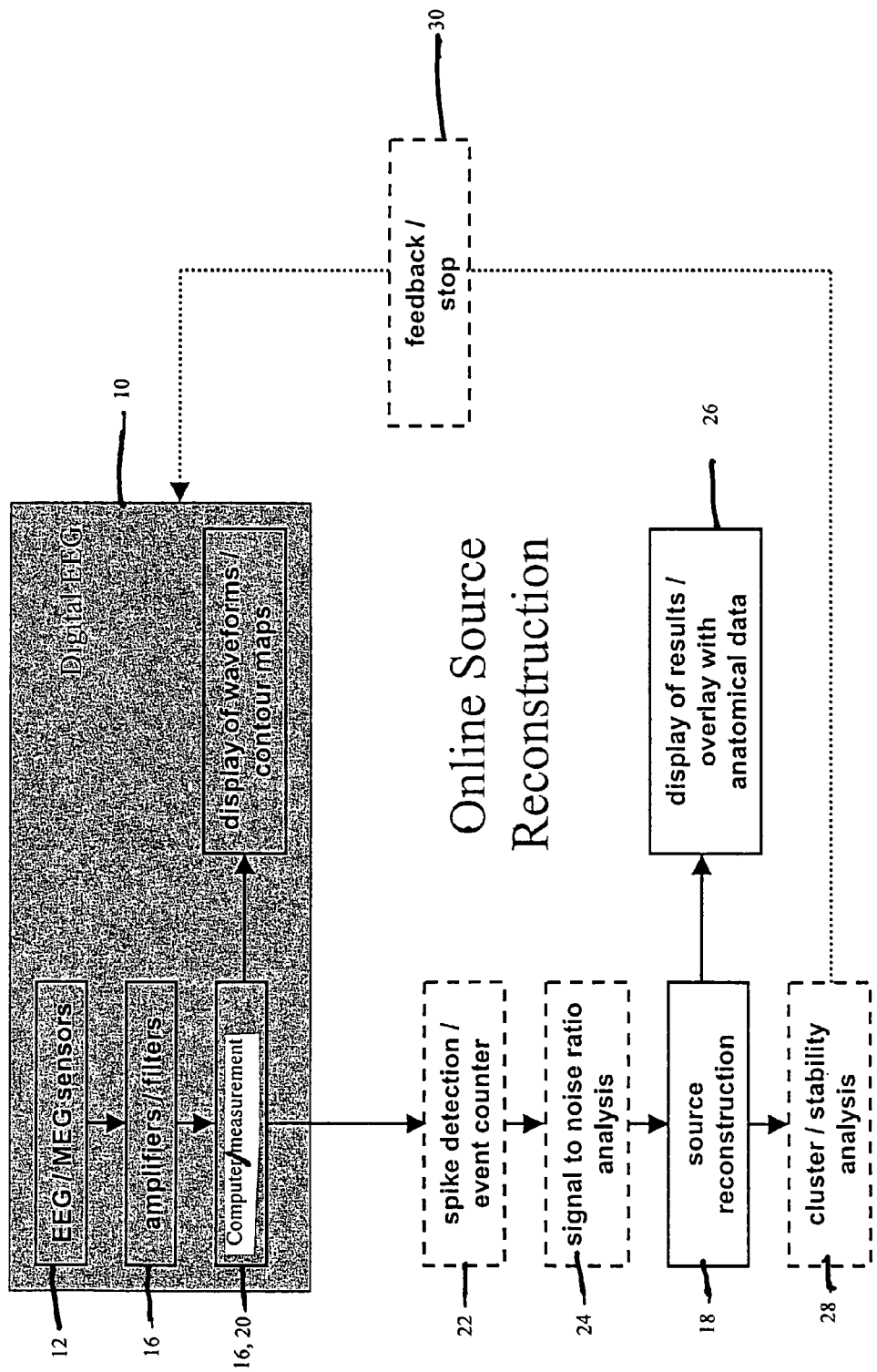

This application claims priority from U.S. Provisional Application No. 60/443,234 filed on Jan. 27, 2003, and hereby incorporated by reference in its entirety.

FIELD OF THE INVENTION

Generally, the invention relates to the field of source imaging. More specifically, the invention relates to performing online source reconstruction for continuously acquired electromagnetic signals.

BACKGROUND OF THE INVENTION

Researchers and doctors often try to locate the source of electromagnetic activity in neural or cardiac tissue in order to diagnose an illness or determine behavioral patterns. The process of source reconstruction is typically used to localize this electromagnetic activity. This process generally involves gathering electromagnetic signals from a patient's neural or cardiac tissue through various modalities such as an electroencephalogram (EEG), magnetoencephalogram (MEG), electrocardiogram (ECG) or magnetocardiogram (MCG). This data is then stored and transported to a stand alone computer system which is used to perform the source reconstruction.

One of the drawbacks to this known method of performing source reconstruction is that it does not provide an indication of the quality of the electromagnetic signals being recorded. A number of variables are involved in determining the source of electromagnetic activity. Errors in the setup of the testing, or a poor signal to noise ratio (SNR) can have a significant impact on the source reconstruction calculation. Flaws in the acquired electromagnetic data may prohibit an acceptable source reconstruction, requiring the patient to repeat the tests. Multiple testing increases the cost of the procedure and makes it more burdensome to the patient.

As a result, there is a need in the art for a method of testing the acquired electromagnetic data to ensure that it can produce a relatively reliable source reconstruction.

SUMMARY OF THE INVENTION

The present invention is a method and apparatus for performing source reconstruction online, wherein an electromagnetic signal undergoes source reconstruction almost immediately after it has been acquired.

In one embodiment, the present invention includes an EEG system comprising of sensors which are utilized to gather an electromagnetic signal from a patient; a signal processing system; and a computer system. The computer system is configured to support multiple threads of execution.

In one embodiment, EEG/MEG sensors acquires an electromagnetic signal from a patient and transmits the signal to the signal processing system. Using known methods, the signal is filtered, amplified, and digitized into data packets which are received by the computer system.

In one embodiment, the computer system initiates a first thread, a measurement module, where the data is filtered and in some cases averaged. Typically, the data is filtered for a particular latency period. Once the data has been filtered and averaged, the result is given to a second thread, the source reconstruction module, which then proceeds to generate a source reconstruction for the trial. The measurement module then acquires and processes new electromagnetic data from a new trial while the source reconstruction is being performed on the most recent trial.

In one embodiment, a feedback loop is in communication with the measurement setup that is acquiring the electromagnetic data. The feedback loop controls the parameters of the acquisition process or stops the measurement after a certain stability criterion is met. Using the results from the source reconstruction, the testing setup can be modified to increase the quality of the acquired electromagnetic signal.

BRIEF DESCRIPTION OF THE DRAWINGS AND FIGURES

For purposes of facilitating and understanding the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

FIG. 1 shows a flowchart of an example of online source reconstruction with a digital EEG setup.

Figure 2:
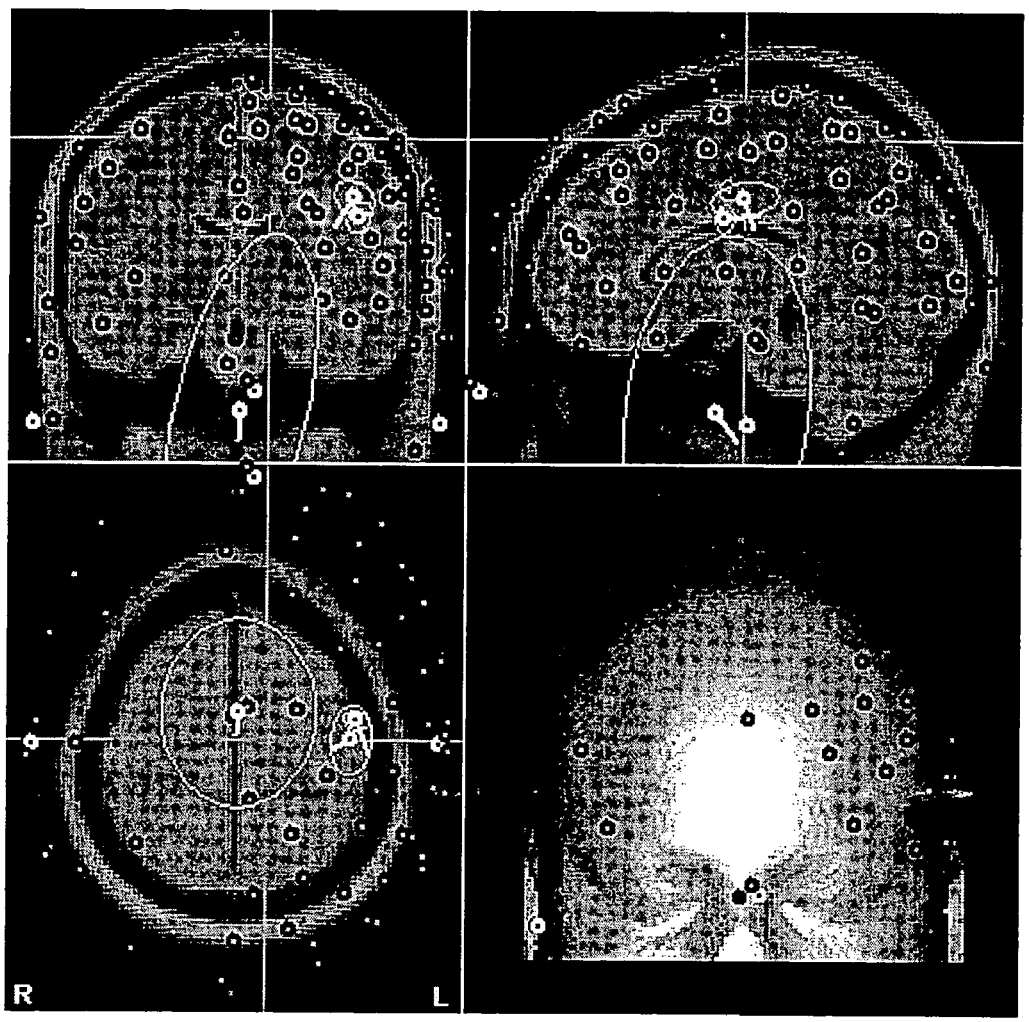

FIG. 2 an example of a scatter plot showing dipole locations.

DETAILED DESCRIPTION OF THE PREFERRED EMBODIMENTS

As shown in FIG. 1, in one embodiment, the present invention is integrated into an EEG system 10. The use of an EEG system 10 is primarily for the purpose of explanation only. One skilled in the art can readily understand that the present invention is easily adapted for use in a number of different applications wherein the tissue source of an electromagnetic signal is being determined.

The EEG system 10 includes sensors 12 which are utilized to acquire an electromagnetic signal from a patient. A signal processing system 14 filters, amplifies, and digitizes the electromagnetic signal. A computer system 16 includes memory storage devices for storing the signal received from the signal processing system 14 and one or more processors for processing the signals. The computer system 16 is configured to support multiple threads of execution. Multiple threads of execution represent a single sequence of instructions executed in parallel with other sequences, either by time slicing or multiprocessing. As opposed to multi-tasking which run essentially independent processes, multiple threads are able to share information, memory and other resources directly between each thread.

In one embodiment, an electromagnetic physiological signal is acquired using a test setup comprising of a plurality of sensors and a signal processing system. The EEG/MEG sensors 12 acquires an electromagnetic signal from a patient and transmits the signal to the signal processing system 14. Using known methods, the signal is filtered, amplified, and digitized into data packets which are received by the computer system 16.

In one embodiment, the measured and digitized data are shared between two integrated threads. One thread includes a source reconstruction module 18 wherein the data is utilized to determine the location of the source tissue and wherein a graphical representation of the source tissue is generated. One example of a compatible source reconstruction module is the SOURCE® software package by Neuroscan. A second thread can include a measurement software module 16 which is capable of analyzing, filtering, mapping, and graphing the acquired signal. One example of a compatible measurement software module is the SCAN® software package by Neuroscan.

In one embodiment, the acquired electromagnetic data goes initially to the measurement module 16 where the data is filtered and in some cases averaged. Typically, the data is filtered for a particular latency period, the latency period being dependent upon the type of testing being done. An epoch or trial length in Somatosensory Evoked Potentials (SEPs) is in the order of 1 second. Sampling rates in this case are in the order of 1 kHz (1 ms sampling time). Once the data has been filtered and averaged, the result is given to the source reconstruction module 18 which then proceeds to generate a source reconstruction for the trial. The measurement module 16 then acquires and processes electromagnetic data from a new trial while the source reconstruction is being performed on the most recent trial.

There are a number of different methods known in the art for performing source reconstruction. Source reconstruction typically involves determining the type of electromagnetic activity, such as a single equivalent current dipole (ECD), a moving dipole, a stationary dipole, a fixed dipole, or a regional dipole, and creating a model which attempts to determine the source of activity through the use of mathematical formulas which describe electromagnetic field distributions of the electromagnetic activity. These models typically depend on the position and orientation of the source, the position and orientation of the sensors which pick up the electromagnetic signals, and the geometry and conductivity properties of the volume conductor (head or chest) tissue. There are several models which are known in the art, these include a three concentric sphere, Boundary Element Method (BEM), and Finite Element Method (FEM) volume conductor models.

Measured data exhibits a limited Signal-to-Noise Ratio (SNR) due to background activity, environmental and amplifier noise. The noise distribution of the data leads to scattered dipole positions in the source space around the most probable source position. As such, the reconstructed dipoles only represent the most probable source positions.

Using online source reconstruction at a certain latency (e.g., 20 ms post stimulus for finger/hand stimulation) the data quality/SNR of the data with respect to source reconstruction/stability can be checked online in real time, since a single moving dipole source reconstruction (using Source V2) takes about 3 ms on a state-of-the-art PC (~2 GHz). The integrated measuring/source localization package (SCAN/SOURCE) is able to reconstruct dipoles at one or several preselected latencies after each measuring epoch/trial after averaging the data. In some instances, several hundred and up to several thousand averages are required in order to improve the SNR of the measurements. Due to enhanced computational performance, optimized algorithms, and software architecture (threads), online source reconstruction for electroencephalography/electrocardiography (EEG/ECG) and/or magnetoencephalography/magnetocardiography (MEG/MCG) becomes possible.

In addition to the source reconstruction, the source reconstruction module may also include known procedures for spike detection/event counting 22, SNR analysis 24, and for overlaying the results on anatomical data 26 (as shown in FIG. 2). In one embodiment, the source reconstruction module first performs an event detection (e.g., for detecting epileptic spikes) or a certain number of averages (e.g., evoked potential for functional mapping) and/or SNR analysis. The source reconstruction functionality is then called, and the results are displayed (e.g., equivalent current dipoles, optional with an overlay to anatomical image data) on a display. Optional result analyses can be added (e.g., cluster analysis for epileptic spikes 28 or confidence volume analysis for functional mapping results.)

The procedure for epileptic spike reconstruction is different, as no averaging of the measured data takes place. Typical sampling rates are in the order of 200 Hz (5 ms). After automated spike detection/thresholding of the ongoing EEG, dipoles can be reconstructed online (source reconstruction is implemented as separate, low priority thread on the acquisition/reconstruction package in order to avoid data loss) for a preselected latency time/range with the same advantages as above and accelerated and improved epileptic focus localization/diagnosis becomes possible.

In one embodiment, a feedback loop 30 is in communication with the measurement setup that is acquiring the electromagnetic data. The feedback loop controls the parameters of the acquisition process or stops the measurement after a certain stability criterion or SNR is met. Online source reconstruction enhances the possibilities of and adds value to digital (e.g., neurophysiological) measurements since it provides immediate feedback over the measurement setup and the data quality as well as the subject/patient condition. With confidence ellipsoids or scatter plots of the dipole locations the increasing stability of the source position due to the increasing SNR can be monitored and systematic setup/configuration errors can be found directly during the testing procedure.

The matter set forth in the foregoing description and accompanying drawings is offered by way of illustration only and not as a limitation. While a particular embodiment has been shown and described, it will be obvious to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A method of evaluation comprising:
   acquiring an electromagnetic physiological signal with a sensor on a subject;
   performing a source reconstruction of the electromagnetic physiological signal via a signal processing circuit in communication with said sensor, with said circuit including a computer system with a processor and a memory, the computer system being configured to support multiple parallel threads of execution with one thread being a measurement module and a second thread being a source reconstruction module;
   feeding source reconstruction data through a feedback loop to the measurement module to modify the analysis of a new electromagnetic physiological signal, wherein the new electromagnetic physiological signal is being acquired while the source reconstruction is being performed; and
   displaying source reconstruction results overlayed onto anatomical data of said patient.

2. The method of claim 1, wherein the sensor acquires MEG data.

3. The method of claim 1, wherein the sensor acquires EEG data.

4. The method of claim 1, wherein the sensor acquires ECG data.

5. The method of claim 1, wherein the sensor acquires MCG data.

* * * * *